United States Patent
Lee et al.

(10) Patent No.: US 6,265,599 B1
(45) Date of Patent: Jul. 24, 2001

(54) PROCESS FOR PREPARING A MIXTURE OF AMINO-CONTAINING PHOSPHAZENES

(75) Inventors: Ching-Yuan Lee; Yie-Shun Chiu, both of Taipei (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 0 days.

(21) Appl. No.: 09/614,752

(22) Filed: Jul. 12, 2000

(51) Int. Cl.$^7$ .................................................. C07F 9/553
(52) U.S. Cl. ........................................ 558/80; 558/157
(58) Field of Search ............................... 558/70, 80, 157

(56) References Cited

U.S. PATENT DOCUMENTS

| | | | |
|---|---|---|---|
| 3,193,571 | * | 7/1965 | Bilger . |
| 3,939,228 | * | 2/1976 | Kao . |
| 4,618,691 | * | 10/1986 | Medina et al. . |
| 5,105,001 | * | 4/1992 | Goins et al. . |

OTHER PUBLICATIONS

CA:112:119103 abstract of Phosphorus, Sulfur Silicon Relat. Elem. by Fincham et al 41(3–4) pp 317–22, year 1989.*

CA:111:154982 abstract of Han'guk Somyu Konghakhoechi by Jeong et al 25(7) pp 553–60, year 1988.*

CA:108131952 abstract of J. Agric. Food Chem. by Peters et al 36(2) pp 384–390, year 1988.*

* cited by examiner

*Primary Examiner*—Jean F. Vollano
(74) *Attorney, Agent, or Firm*—Bacon & Thomas, PLLC

(57) ABSTRACT

The present invention provides a process for preparing a mixture of amino-containing phosphazenes having the following general formula (I) by reacting a $(NPCl_2)_n$ phosphazene mixture with $NH_3$ and HOR in the presence of a tertiary amine catalyst:

$$N_nP_n(NH_2)_x(OR)_{2n-x} \tag{I}$$

wherein $n \geq 3$, $1 \leq x < 2n$, and R is phenyl or C3–C6 alkyl. In addition to simultaneously carrying out amination and esterification, the process of the present invention also simultaneously performs a regeneration of the catalyst. Furthermore, the invented process is a water-free process without the problem of a large quantity of waste water. Ammonium chloride, a by-product of the invented process, can be recovered in a subsequent process.

12 Claims, 1 Drawing Sheet

PROCESS FOR PREPARING A MIXTURE OF AMINO-CONTAINING PHOSPHAZENES

FIELD OF THE INVENTION

The present invention relates to a process for preparing a mixture of amino-containing phosphazenes that can be used simultaneously as a curing agent and a flame retardant for resins, particularly to a water-free process for preparing an mixture of amino-containing phosphazenes.

BACKGROUND OF THE INVENTION

Phosphazenes are compounds that contain —P=N— bonds and have a general formula $[NPR'R'']_n$, wherein n is $\geq 3$. Such compounds have thousands of derivatives along with a change in R' and R''. In addition to a variation in R' and R'', the structures of the phosphazenes can be classified into cyclic compounds and linear compounds. When n=3, the compounds become benzene-like hexagonal planar compounds. When n=4, the compounds become octangular cyclic compounds. Among the identified cyclic phosphazenes, the maximum n value is 10. Phosphazenes with $n \geq 3$ can also exist in a linear form. Phosphazenes have always been viewed as a potential flame retardant in view of a synergistic effect of P and N elements. When R' or R'' is a group containing an active hydrogen (such as amino or hydroxyl), such phosphazenes can even be used to cure a resin having functional group(s) that can react with an active site, such as polyurethane having isocyanate terminals and epoxy resins. A typical example of the amino-containing phosphazene that can be used as a curing agent and a flame retardant for the polyurethane and epoxy resins, has a structure of $N_nP_n(NH_2)_x(OR)_{2n-x}$, wherein $1 \leq x < 2n$, and R is phenyl or C3–C6 alkyl. The conventional processes for preparing such amino-containing phosphazenes basically can be classified into two types. The first type of preparation process comprises amination and then esterification; and the second type of preparation process comprises esterification and then amination. The following Scheme 1 shows an example of the first type, in which $N_3P_3(NH_2)_2(OC_3H_7)_4$ is synthesized:

Scheme 1

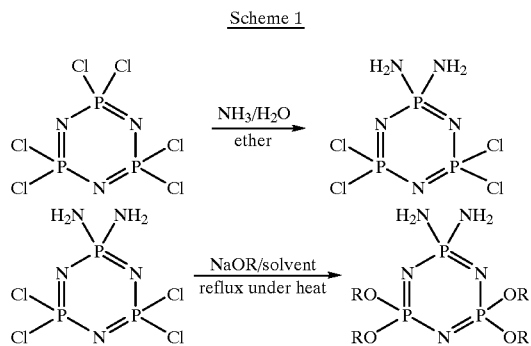

Scheme 2

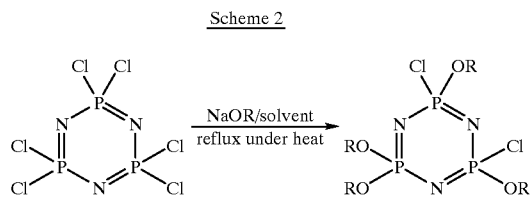

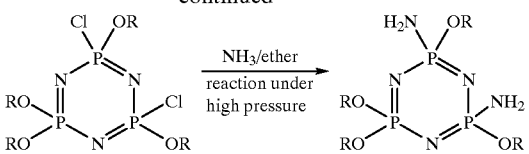

In Scheme 2, the amination step can only be completed under a pressurized state, which increases the complexity and the safety concerns of the process.

The above-mentioned processes all have a defect of having too many operational steps thereof. Take Scheme 1 as an example:
Step 1: amination;
step 2: separating the organic phase from the aqusous phase after the amination;
step 3: removing the organic solvent by evaporation, thereby obtaining $N_3P_3(NH_2)_2Cl_4$;
step 4: reacting the intermediate product $N_3P_3(NH_2)_2Cl_4$ with $NaOC_3H_7$ under refluxing;
Step 5: after reaction, washing off NaCl with water; and separating the organic phase from the aqueous phase;
Step 6: drying off residual moisture in the organic phase; and
Step 7: removing the organic solvent from the organic phase by evaporation, thereby obtaining the product.

SUMMARY OF THE INVENTION

The present invention provides a process for preparing a mixture of amino-containing phosphazenes having the following general formula (I) via simultaneous amination and esterification by reacting a $(NPCl_2)_n$ phosphazene mixture with $NH_3$ and HOR in the presence of a tertiary amine catalyst:

$$N_nP_n(NH_2)_x(OR)_{2n-x} \qquad (I)$$

wherein $n \geq 3$, $1 \leq x < 2n$, and R is phenyl or C3–C6 alkyl.

In addition to simultaneously carrying out amination and esterification, the process according to the present invention also simultaneously performs a regeneration of the catalyst. Therefore, the invented process not only greatly reduces the operational steps, but also the reaction time. Moreover, the invented process is a water-free process without the problem of a large quantity of waste water and sodium chloride. Furthermore, a by-product, ammonium chloride, of the invented process, can be recovered in a subsequent process.

DETAILED DESCRIPTION OF THE INVENTION

Figure 1:
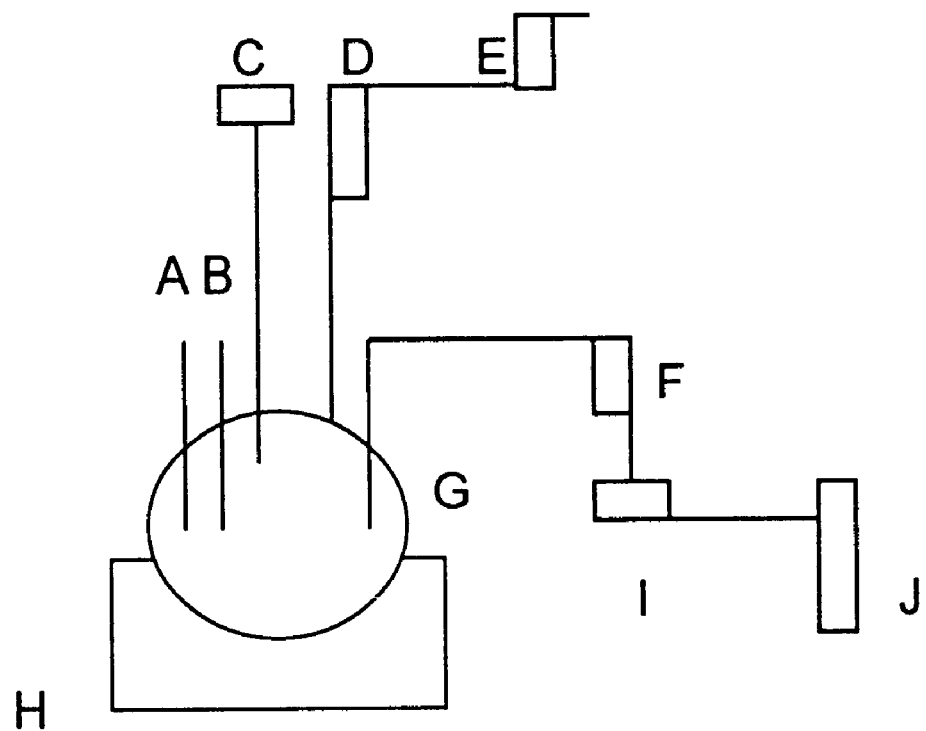
FIG. 1 shows a schematic view of a reaction system suitable for use in the invented process.

The present invention discloses a process for preparing a mixture of amino-containing phosphazenes having the following formula (I):

$$N_nP_n(NH_2)_x(OR)_{2n-x} \qquad (I)$$

wherein n is an integer and $n \geq 3$;
x is an integer of $1 \leq x$ x<2n; and
R is phenyl or $C_3$–$C_6$ alkyl, preferably R is propyl.
Said process comprises the following steps:
a) introducing $NH_3$ into a reactant mixture comprising HOR, mixed phosphazenes of $(NPCl_2)_n$ and a tertiary amine to undergo reactions at a temperature of 30–100° C. for a period of time;

b) removing a solid comprising NH$_4$Cl precipitate from the resulting reaction mixture from step a) by a solid-liquid separation means; and c) removing volatile compounds from the resulting liquid from step b) by evaporation to obtain a mixed product consisting essentially of amino-containing phosphazenes having the formula (I).

Preferably, the reactant mixture used in step a) of the invented process further comprises an organic solvent, preferably chlorobenzene.

Preferably, the mixed phosphazenes of (NPCl$_2$)$_n$ in step a) comprise 60–70% by mole of phosphazenes where n=3; 10–20% by mole of phosphazenes where n=4; and 10–20% by mole of phosphazenes where n≥5.

Preferably, the tertiary amine in step a) of the invented process is pyridine.

Preferably, the reactant mixture in step a) of the invented process comprises 100–500 parts by weight of phosphazenes, 20–150 parts by weight of pyridine, and 500–2000 parts by weight of HOC$_3$H$_7$. More preferably, said mixture comprises 350 parts by weight of phosphazenes, 40–80 parts by weight of pyridine, and 1000 parts by weight of HOC$_3$H$_7$.

When the reactant mixture of step a) further comprises chlorobenzene, said reactant mixture of step a) preferably comprises 100–500 parts by weight of phosphazenes, 80–360 parts by weight of pyridine, 300–2400 parts by weight of HOC$_3$H$_7$, and 500–3600 parts by weight of chlorobenzene. More preferably, the reactant mixture of step a) comprises 350 parts by weight of phosphazenes, wherein the part by weight of chlorobenzene is not less than that of HOC$_3$H$_7$.

The present invention will be further disclosed through the following example. The example is for illustrative purposes only and not for limiting the scope of the present invention.

EXAMPLE

In this example, the reaction for the synthesis of N$_n$P$_n$(NH$_2$)$_x$(OC$_3$H$_7$)$_{2n-x}$ can be shown by the following:

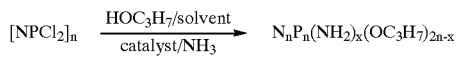

since the product is to be used for the curing of epoxy and polyurethane resins, each molecule needs to have at least two NH$_2$ groups. Because the synthesized product is not a single amino-containing phosphazene, such as a pure N$_3$P$_3$(NH$_2$)$_2$(OC$_3$H$_7$)$_4$, but is a mixture of N$_n$P$_n$(NH$_2$)$_x$(OC$_3$H$_7$)$_{2n-x}$. Therefore, this example will show the effect of reaction conditions on the x value.

This example uses a reaction system, as shown in FIG. 1, which comprises a reaction bottle G placed on a thermostat H. Said reaction bottle G is equipped with a thermometer insertion tube A, a feed tube B, a mechanical stirrer C, a said condenser D. Said an inlet tube for NH$_3$ gas, wherein an NH$_3$ gas cylinder J is connected to said inlet tube for NH$_3$ gas and a washing tower E is connected to said condenser D. Said inlet tube for NH$_3$ gas is installed with a needle valve I for flow control and a flow meter F.

Pyridine (abbreviated as Py hereinafter), chlorobenzene (abbreviated as CB hereinafter), n-Propanol (abbreviated as NPA hereinafter) were fed to the reaction bottle G according to a predetermined stoichiometric ratio. A phosphazene mixture of (NPCl$_2$)$_n$ (consisting of 60–70% by mole of phosphazene where n=3; 10–20% by mole of phosphazene where n=4; and 10–20% by mole of phosphazene where n≥5) was added within 30 minutes. The temperature of the reaction liquid is maintained at 25–35° C. Upon completion of the addition of (NPCl$_2$)$_n$, an NH$_3$ gas was introduced according to predetermined flow rates, and the thermostat was used to maintain the reaction temperature according to the following schedule:

| | |
|---|---|
| Stage one 40° C. | 2 hours |
| Stage two 50° C. | 2 hours |
| Stage three 60° C. | 2 hours |
| Stage four 70° C. | 1 hour |

Upon completion of the reaction, the introduction of NH$_3$ was stopped, and the reaction mixture was allowed to cool down to room temperature without disturbance. Then, the solid ammonium chloride was filtered out, and the liquid part was subjected to removal of Py, CB and NPA by evaporation at a temperature of 90° C. and a pressure of 30–40torr, thereby obtaining a brown product.

The amination and esterification of the reaction mixture were monitored by using IR spectrum. The results show that the substituents of —NH$_2$ and —OC$_3$H$_7$ absorption peaks appeared within the first hour after the commencement of the reactions. This indicates that the reactions of the esterification and amination take place simultaneously. The relative positions of the absorption peaks of the two substituents do not vary much after four hours of reaction, which indicates that the main substitution reactions have been completed.

N$_n$P$_n$(NH$_2$)$_x$(OC$_3$H$_7$)$_{2n-x}$ contains —NH$_2$ and —OC$_3$H$_7$ groups, and shows IR absorption peaks of ν N—H 3270cm$^{-1}$ and ν-C—H 2965cm$^{-1}$, respectively. The intensities of the absorption peaks are related to x and 2n–x values. A larger x value indicates a larger amount of —NH$_2$ groups present, and vice versa. Therefore, the ratio of the two absorption peaks can be used to estimate the degree of amination. Table 1 shows elemental analysis of the related amino- containing phosphazenes.

TABLE 1

| Molecular formula | MW | P % | Cl % | C % | H % | N % |
|---|---|---|---|---|---|---|
| N$_3$P$_3$(NH$_2$)$_1$(OC$_3$H$_7$)$_5$ | 446 | 20.85 | 0 | 40.35 | 8.30 | 12.55 |
| N$_3$P$_3$(NH$_2$)$_2$(OC$_3$H$_7$)$_4$ | 403 | 23.08 | 0 | 35.73 | 7.94 | 17.37 |
| N$_3$P$_3$(NH$_2$)$_2$(OC$_3$H$_7$)$_3$Cl | 379.5 | 24.50 | 9.35 | 28.46 | 6.59 | 18.40 |
| N$_3$P$_3$(NH$_2$)$_3$(OC$_3$H$_7$)$_3$ | 360 | 25.83 | 0 | 30.00 | 7.50 | 23.33 |
| N$_3$P$_3$(NH$_2$)$_3$(OC$_3$H$_7$)$_4$Cl | 336.5 | 27.64 | 10.55 | 21.39 | 5.94 | 24.96 |
| N$_4$P$_4$(NH$_2$)$_2$(OC$_3$H$_7$)$_6$ | 566 | 21.91 | 0 | 38.16 | 8.13 | 14.84 |
| N$_4$P$_4$(NH$_2$)$_3$(OC$_3$H$_7$)$_5$ | 523 | 23.70 | 0 | 34.42 | 7.84 | 18.73 |

Table 2 lists the influence of the flow rate of NH$_3$ gas, the amount of CB solvent, and the amount of Py on the degree of amination of the product.

TABLE 2

| Run | Py | NPA | CB | Flow rate of NH₃*time | Ratio of IR absorption peaks of $NH_2/OC_3H_7$ | P% | Cl% | C% | H% | N% |
|---|---|---|---|---|---|---|---|---|---|---|
| 1 | 50 | 360 | 700 | 8*15 min<br>4*15 min<br>16*25 min<br>4*20 min<br>3*90 min<br>2*175 min | 56.9% | 21.64 | 2.54 | | | |
| 2 | 50 | 360 | 700 | 8*10 min<br>16*170 min<br>4*90 min<br>2*80 min | 85.7% | 23.86 | 2.23 | | | |
| 3 | 50 | 360 | 700 | 4*10 min<br>16*200 min<br>2*110 min | 93.4% | 23.74 | 2.41 | | | |
| 5 | 50 | 360 | 700 | 4*435 min | 68.4% | 23.82 | 2.88 | 31.4 | 7.2 | 18.4 |
| 6 | 50 | 360 | 700 | 4*162 min<br>2*240 min<br>1*50 min | 31.7% | 21.32 | 1.74 | 38.1 | 8.0 | 13.0 |
| 7 | 50 | 360 | 700 | 2*420 min | 54.9 % | 22.60 | 3.45 | 34.3 | 7.5 | 14.6 |

Note:
1. The amount of $(NPCl_2)_n$ in each run is 348 g.
2. Flow rate of $NH_3$ gas: The values in the table are scale values of the flow meter. The corresponding actual flow rates are:

| Scale value | Actual flow rate (ml/min) | Scale value | Actual flow rate (ml/min) |
|---|---|---|---|
| 1 | 82 | 10 | 655 |
| 2 | 144 | 12 | 720 |
| 4 | 320 | 14 | 840 |
| 6 | 428 | 16 | 930 |
| 8 | 560 | 20 | 1036 |

The relationship between the flow rate and the scale value is:

Flow rate$=-1.3531x^2+78.612x+4.5309$, wherein x is the scale value.

According to the content of the phosphorus element and the ratio of the IR absorption peaks in Table 1 and Table 2, the ratio of the IR absorption peaks shall exceed 60%, and the content of phosphorus is about 22–24 wt %, when there are two —$NH_2$ groups in the amino-containing phosphazenes.

A gas chromatograph (GC) was used to measure the relative contents of CB and NPA during the reactions in three experiment runs, and the results are listed in Table 3. The data in Table 3 indicate that the reactions are substantially completed-in five hours. This conclusion conforms nicely with the variation of the IR absorption peaks.

TABLE 3

Tracing the relative content of NPN/CB in the reaction liquid by GC

| Reaction time (hour) | Reaction one NPA % | Reaction two NPA % | Reaction three NPA % |
|---|---|---|---|
| 0 | 42.75 | 43.85 | 36.83 |
| 1 | 34.47 | 35.10 | 32.74 |
| 2 | 30.30 | 32.21 | 25.74 |
| 3 | | 29.95 | 23.37 |
| 4 | 32.39 | 29.49 | 22.67 |
| 5 | | 28.45 | 21.06 |
| 6 | 31.579 | 28.99 | 20.39 |
| 7 | | | 20.34 |
| 8 | | | |
| 9 | 31.10 | 28.41 | 21.14 |

In order to understand the influence of the flow rate of the $NH_3$ gas, the solvent, and the amount of Py on the degree of amination of the product, more experiment runs were carried out. The results and the reaction conditions are listed in Table 4.

TABLE 4

| Run | Py | NPA | time | CB | Flow rate of $NH_3$ gas*<br>Ratio of IR absorption peaks of $NH_2OC_3H_7$ | P% | Cl% | C% | H% | N% |
|---|---|---|---|---|---|---|---|---|---|---|
| 1A | 80 | 1000 | 0 | | 2*420 min    <10% | 21.13 | 4.42 | 37.1 | 7.6 | 10.8 |
| 1B | 80 | 500 | 500 | | 2*420 min    <10% | 19.69 | 4.27 | 38.7 | 7.4 | 10.3 |

TABLE 4-continued

| Run | Py | NPA | time | Flow rate of NH₃ gas* CB | Ratio of IR absorption peaks of NH₂OC₃H₇ | P% | Cl% | C% | H% | N% |
|---|---|---|---|---|---|---|---|---|---|---|
| 2A | 80 | 1000 | 0 | 6*420 min | 48.4% | 21.40 | 0.67 | 38.0 | 82 | 14.1 |
| 2B | 80 | 500 | 500 | 6*420 min | 69.7% | 21.54 | 1.13 | 36.1 | 8.0 | 16.5 |
| 3A | 160 | 1000 | 0 | 2*420 min | 29.0% | 19.62 | 0.42 | 42.0 | 8.5 | 10.0 |
| 3B | 80 | 300 | 700 | 6*420 min | 73.5% | 23.60 | 1.66 | 35.5 | 7.7 | 17.1 |
| 4A | 160 | 1000 | 0 | 6*360 min<br>2*60 min | 41.0% | 20.76 | 0.97 | 39.41 | 12.5 | 8.3 |
| 5A | 240 | 1000 | 0 | 6*360 min<br>2*60 min | 17.1% | 19.60 | 0.40 | 40.8 | 8.5 | 11.0 |
| 6A | 160 | 1000 | 0 | 6*360 min<br>2*60 min | 40.0% | 20.39 | 0.44 | 38.6 | 8.3 | 13.0 |
| 7A | 80 | 1000 | 0 | 8*300 min<br>4*10 min<br>2*95 min | 60.4% | 23.06 | 1.06 | 33.5 | 7.8 | 18.1 |
| 8A | 80 | 1000 | 0 | 10*240 min<br>6*120 min<br>2*60 min | 63.4% | 23.06 | 1.33 | 32.3 | 7.7 | 18.9 |
| 9A | 80 | 1000 | 0 | 8*300 min<br>4*25 min<br>2*120 min | 55.5% | 22.34 | 0.66 | 35.0 | 8.0 | 17.4 |
| 10A | 80 | 1000 | 0 | 10*160 min<br>4*80 min<br>2*180 min | 78.6% | 22.90 | 1.38 | 33.0 | 7.8 | 19.0 |
| 11A | 40 | 1000 | 0 | 6*420 min | 75.0% | 23.42 | 1.30 | 31.1 | 7.1 | 18.6 |
| 12B | 180 | 1200 | 1800 | 18*360 min<br>4*60 min | 70.0% | 22.50 | 1.63 | 32.4 | 7.6 | 19.4 |
| 13B | 360 | 2400 | 3600 | 20*195 min<br>15*90 min<br>10*155 min | 51.0% | 19.56 | 3.36 | 39.1 | 7.2 | 13.7 |
| 14B | 360 | 2400 | 3600 | 25*130 min<br>20*210 min<br>15*20 min<br>10*60 min | 68.6% | 23.48 | 1.24 | 34.0 | 7.7 | 18.1 |
| 15A | 80 | 1000 | 0 | 20*250 min<br>8*170 min | 83.0% | 23.46 | 1.72 | 31.7 | 7.7 | 20.1 |

Notes:
1. The amount of (NPCl₂)ₙ used in each run is 348 g.

2. The experiment Run 12B used a 5-liter reaction bottle; the experiment Runs 13B and 14B used a 12-liter reaction bottle; and the rest of the experiment runs use a 3-liter reaction bottle.

3. The flow rate meter used in experiment Runs 1–12 and 15 is identical to that used in Table 2. Experiment Runs 1 3B and 14B used another flow rate meter, in which the relationship between the scale and the flow rate thereof is:

| Scale | Flow rate (ml/min) |
|---|---|
| 10 | 854 |
| 15 | 1500 |
| 20 | 2180 |
| 25 | 2878 |

The relationship between the flow rate and the scale is: flow rate=1 35.24X–513.2, wherein X is the scale value.

What is claimed is:

1. A process for preparing a mixture of amino-containing phosphazenes having the following formula (I):

$$N_nP_n(NH_2)_x(OR)_{2n-x} \quad (I)$$

wherein n is an integer and n≧3;
x is an integer of 1≦x≦2n; and
R is phenyl or $C_3$–$C_6$ alkyl, said process comprising the following steps:
a) introducing NH₃ into a reactant mixture comprising HOR, mixed phosphazenes of (NPCL₂)ₙ and a tertiary amine to undergo reactions at a temperature of 30–100° C. for a period of time, wherein n is defined as above;
b) removing a solid comprising NH₄Cl precipitate from the resulting reaction mixture from step a) by a solid-liquid separation means; and
c) removing volatile compounds from the resulting liquid from step b) by evaporation to obtain a mixed product consisting essentially of amino-containing phosphazenes having the formula (I).

2. The process according to claim 1, wherein R is —$C_3H_7$ alkyl.

3. The process according to claim 2, wherein the reactant mixture used in step a) further comprises an organic solvent.

4. The process according to claim 1, wherein the mixed phosphazenes of (NPCl₂)ₙ in step a) comprise 60–70% by mole of phosphazenes where n=3; 10–20% by mole of phosphazenes where n=4; and 10–20% by mole of phosphazenes where n≧5.

5. The process according to claim 1, wherein the tertiary amine in step a) is pyridine.

6. The process according to claim 2, wherein the tertiary amine in step a) is pyridine.

7. The process according to claim 3, wherein the tertiary amine in step a) is pyridine.

8. The process according to claim 7, wherein said organic solvent is chlorobenzene.

9. The process according to claim 6, wherein the reactant mixture in step a) comprises 100–500 parts by weight of the mixed phosphazenes, 20–150 parts by weight of pyridine, and 500–2000 parts by weight of $HOC_3H_7$.

10. The process according to claim 9, wherein the reactant mixture in step a) comprises 350 parts by weight of the mixed phosphazenes, 40–80 parts by weight of pyridine, and 1000 parts by weight of $HOC_3H_7$.

11. The process according to claim 8, wherein the reactant mixture in step a) comprises 100–500 parts by weight of the mixed phosphazenes, 80–360 parts by weight of pyridine, 300–2400 parts by weight of $HOC_3H_7$, and 500–3600 parts by weight of chlorobenzene.

12. The process according to claim 9, wherein the reactant mixture in step a) comprises 350 parts by weight of phosphazenes, wherein the part by weight of chlorobenzene is not less than that of $HOC_3H_7$.

* * * * *